(12) United States Patent
Yunoki

(10) Patent No.: US 7,005,542 B2
(45) Date of Patent: Feb. 28, 2006

(54) CATALYST FOR SYNTHESIS OF UNSATURATED ALDEHYDE, PRODUCTION PROCESS FOR SAID CATALYST, AND PRODUCTION PROCESS FOR UNSATURATED ALDEHYDE USING SAID CATALYST

(75) Inventor: Hiromi Yunoki, Himeji (JP)

(73) Assignee: Nippon Shokubai Co., Ltd., Osaka (JP)

(*) Notice: Subject to any disclaimer, the term of this patent is extended or adjusted under 35 U.S.C. 154(b) by 0 days.

(21) Appl. No.: 10/358,796

(22) Filed: Feb. 5, 2003

(65) Prior Publication Data

US 2003/0162998 A1    Aug. 28, 2003

(30) Foreign Application Priority Data

Feb. 28, 2002 (JP) .............................. 2002-054488

(51) Int. Cl.
*C07C 51/16* (2006.01)

(52) U.S. Cl. ...................... 562/537; 562/538; 562/545; 568/431

(58) Field of Classification Search ................ 562/512, 562/512.2, 517, 521, 523, 531, 537, 538, 562/542, 544, 546, 547, 549; 568/420, 448, 568/444, 469.9, 470

See application file for complete search history.

(56) References Cited

U.S. PATENT DOCUMENTS

| | | | |
|---|---|---|---|
| 3,972,920 A | 8/1976 | Ishii et al. | |
| 5,856,259 A | 1/1999 | Watanabe et al. | |
| 5,892,108 A | 4/1999 | Shiotani et al. | |
| 5,981,804 A | 11/1999 | Kurimoto et al. | |
| 6,525,217 B1 | 2/2003 | Unverricht et al. | |

FOREIGN PATENT DOCUMENTS

| | | |
|---|---|---|
| DE | 199 10 506 A1 | 9/2000 |
| EP | 0 304 867 A2 | 3/1989 |
| EP | 0 807 465 A1 | 11/1997 |
| EP | 1 052 017 A2 | 11/2000 |
| GB | 2030885 * | 9/1978 |
| GB | 2 030 885 A | 4/1980 |
| JP | 50-13308 B | 2/1975 |
| JP | 50-47915 A | 4/1975 |
| JP | 56-23969 B2 | 6/1981 |
| JP | 64-56634 A | 3/1989 |
| JP | 5-253480 A | 10/1993 |
| JP | 8-238433 A | 9/1996 |
| JP | 9-10587 A | 1/1997 |
| JP | 2001-96162 A | 4/2001 |
| JP | 2002-539102 A | 11/2002 |
| WO | WO 00/53558 A1 | 9/2000 |

* cited by examiner

*Primary Examiner*—Johann Richter
*Assistant Examiner*—Karl Puttlitz

(57) ABSTRACT

The present invention provides: a production process for a catalyst for synthesis of an unsaturated aldehyde and/or an unsaturated carboxylic acid, which production process is suitable for producing the catalyst with good reproducibility, wherein the catalyst is excellent in activity, selectivity, and physical strength; this catalyst; and a production process for the unsaturated aldehyde and/or the unsaturated carboxylic acid by using this catalyst. The production process for the catalyst comprises the steps of: carrying out heat treatment of an aqueous solution or slurry of a starting material to thus prepare a catalyst precursor P1, wherein the starting material includes molybdenum, bismuth, and iron as essential components; thereafter adding and mixing a binder into the P1 to thus prepare a catalyst precursor P2; and molding and then calcining the P2, thereby producing the catalyst for synthesis of the unsaturated aldehyde and/or the unsaturated carboxylic acid; with the production process being characterized by involving an ignition loss ratio of the catalyst precursor P1 in the range of 10 to 40 mass % (excluding 40 mass %).

3 Claims, No Drawings

`CATALYST FOR SYNTHESIS OF UNSATURATED ALDEHYDE, PRODUCTION PROCESS FOR SAID CATALYST, AND PRODUCTION PROCESS FOR UNSATURATED ALDEHYDE USING SAID CATALYST`

BACKGROUND OF THE INVENTION

A. Technical Field

The present invention relates to: a production process for a catalyst for synthesis of an unsaturated aldehyde and/or an unsaturated carboxylic acid; this catalyst; and a production process for the unsaturated aldehyde and/or the unsaturated carboxylic acid by using this catalyst. More particularly, the present invention relates to: a production process for a catalyst for synthesis of an unsaturated aldehyde and/or an unsaturated carboxylic acid, which production process is suitable for producing the catalyst with good reproducibility, wherein the catalyst is excellent in activity, selectivity, and physical strength; a catalyst as obtained by this production process; and a process comprising the step of carrying out catalytic gas phase oxidation of at least one compound selected from the group consisting of propylene, isobutylene, t-butyl alcohol, and methyl t-butyl ether as a raw material with molecular oxygen or a molecular-oxygen-containing gas in the presence of the above catalyst, thereby producing the unsaturated aldehyde and/or the unsaturated carboxylic acid.

B. Background Art

Proposed are a lot of improved catalysts for carrying out catalytic gas phase oxidation of at least one compound selected from the group consisting of propylene, isobutylene, t-butyl alcohol, and methyl t-butyl ether, thereby efficiently producing an unsaturated aldehyde and/or an unsaturated carboxylic acid that correspond to each.

For example, JP-A-013308/1975 and JP-A-047915/1975 disclose catalysts that include Mo, Bi, Fe, Sb, and Ni, and further include at least one element selected from among K, Rb, and Cs as an essential component. JP-A-056634/1989 discloses catalysts that include Mo, Bi, and Fe, and further include at least one element selected from among Ni and Co as an essential component. JP-B-023969/1981 discloses catalysts that include Mo, Bi, and Fe, and further include at least one element selected from IIA and IIB groups as an essential component.

As to the industrial use of the aforementioned catalysts, heat-exchange-type shell-and-tube reactors are generally used. However, the catalysts are packed while being dropped in a reaction tube having a length of several meters to ten and several meters wherein the reaction tube is settled in the above reactor, and therefore it is necessary that the above catalyst should also have sufficient physical strength together in addition to the high activity and the selectivity of the objective product.

In addition, on an industrial scale, catalysts are necessary in large quantities of several tons to dozens of tons, and therefore a person with ordinary skill in the art would sufficiently recognize that: as to a catalyst as produced twice or more, the less the scatter of its activity, selectivity of the objective product, and physical strength is (the better their reproducibility is), the more favorable it is.

From such a point of view, there are also proposed a lot of processes for producing a catalyst with good reproducibility, wherein the catalyst is excellent in activity, selectivity of the objective product, and physical strength.

For example, JP-A-253480/1993 discloses a process that involves carrying out salt decomposition in such a manner that the layer height of not less than 30 weight % of a dried product of catalyst is not lower than 20 mm in a calcination stage. JP-A-238433/1996 discloses a process that involves supporting a catalyst precursor on an inert support, wherein a nitrate radical component and an ammonium radical component are removed from the catalyst precursor by carrying out heat treatment in the temperature range of 200 to 400° C. JP-A-010587/1997 discloses a process that involves carrying out salt decomposition of a dried product as a catalyst precursor by gradually adding it into a flowing gas that is maintained in the temperature range of 200 to 450° C., and thereafter molding and then calcining the resultant decomposed product. JP-A-096162/2001 discloses a process that involves molding and then calcining a powder of a catalyst precursor having an ignition loss ratio of 1 to 5% after the ignition.

The above hitherto proposals (JP-A-253480/1993, JP-A-238433/1996, JP-A-010587/1997, and JP-A-096162/2001) as to the production process for a catalyst all relate to a process that involves removing a salt (e.g. nitrate salts and ammonium salts contained (remaining) in the catalyst precursor) from the catalyst. In these proposals, for example, JP-A-010587/1997 points out that the ammonium salts remaining in the catalyst cause the scatter of chemical and physical properties of the catalyst. In addition, JP-A-096162/2001 points out that the salts and various radical components in the catalyst precursor have an influence on the catalyst performance.

However, there is a problem such that: the catalysts as produced by these hitherto processes have been still insufficient in the activity, the selectivity of the objective product, and the physical strength from the industrial viewpoint, or the reproducibility is lacking for the catalyst production. Therefore, it is desired to further improve the catalysts.

SUMMARY OF THE INVENTION

A. Object of the Invention

Accordingly, an object of the present invention is to provide a production process for a catalyst for synthesis of an unsaturated aldehyde and/or an unsaturated carboxylic acid, which production process is suitable for producing the catalyst with good reproducibility, wherein the catalyst is excellent in activity, selectivity, and physical strength. Another object of the present invention is to provide a catalyst as obtained by this production process. Yet another object of the present invention is to provide a process comprising the step of carrying out catalytic gas phase oxidation of at least one compound selected from the group consisting of propylene, isobutylene, t-butyl alcohol, and methyl t-butyl ether as a raw material with molecular oxygen or a molecular-oxygen-containing gas in the presence of the above catalyst, thereby producing the corresponding unsaturated aldehyde and/or unsaturated carboxylic acid.

B. Disclosure of the Invention

The present inventor has diligently studied in order to solve the above-mentioned problems. As a result, he has found out that: surprisingly, contrary to the above hitherto known information, rather in the case where a catalyst precursor as used when it is molded into a shape as actually used as a catalyst is allowed to contain a salt (e.g. nitrate salts and ammonium salts) in a definite amount range, the resultant catalyst is more excellent than conventional catalysts as produced by conventional processes in respect of the catalyst performance and physical strength, and further the reproducibility in the catalyst production is also enhanced.

Furthermore, the present inventor has also found out that there is no problem in moldability if the amount of water as added to the above catalyst precursor is adjusted in a specific range.

The present invention has been completed in the above way.

That is to say, a production process for a catalyst for synthesis of an unsaturated aldehyde and/or an unsaturated carboxylic acid, according to the present invention, comprises the steps of: carrying out heat treatment of an aqueous solution or slurry of a starting material to thus prepare a catalyst precursor P1, wherein the starting material includes molybdenum, bismuth, and iron as essential components; thereafter adding and mixing a binder into the P1 to thus prepare a catalyst precursor P2; and molding and then calcining the P2, thereby producing the catalyst for synthesis of the unsaturated aldehyde and/or the unsaturated carboxylic acid; with the production process being characterized by involving an ignition loss ratio of the catalyst precursor P1 in the range of 10 to 40 mass % (excluding 40 mass %).

Hereupon, when the catalyst precursor P1 is uniformly mixed and about 10 g thereof is accurately weighed out and then heated under air atmosphere at 300° C. for 1 hour, the ignition loss ratio of the catalyst precursor is calculated from the following equation:

ignition loss ratio (mass %)=(mass of catalyst precursor−mass of catalyst precursor after heating)/mass of catalyst precursor×100.

Furthermore, water is favorably added and mixed as the binder in an amount of 5 to 30 parts by mass relative to 100 parts by mass of the catalyst precursor P1.

In addition, a catalyst for synthesis of an unsaturated aldehyde and/or an unsaturated carboxylic acid, according to the present invention, is obtained by the above production process according to the present invention.

Furthermore, a production process for an unsaturated aldehyde and/or an unsaturated carboxylic acid, according to the present invention, comprises the step of carrying out catalytic gas phase oxidation of at least one compound selected from the group consisting of propylene, isobutylene, t-butyl alcohol, and methyl t-butyl ether as a raw material with molecular oxygen or a molecular-oxygen-containing gas, thereby producing the unsaturated aldehyde and/or the unsaturated carboxylic acid which correspond to the raw material; with the production process being characterized by using the above catalyst according to the present invention.

These and other objects and the advantages of the present invention will be more fully apparent from the following detailed disclosure.

DETAILED DESCRIPTION OF THE INVENTION

As to the catalyst that is used in the present invention and includes molybdenum, bismuth, and iron as essential components, any catalyst can be used if the use thereof makes it possible to produce the corresponding unsaturated aldehyde and/or unsaturated carboxylic acid by the catalytic gas phase oxidation of at least one compound selected from the group consisting of propylene, isobutylene, t-butyl alcohol, and methyl t-butyl ether as a raw material. However, favorably used is a complex-oxide catalyst of a general formula (1) below:

$$Mo_a W_b Bi_c Fe_d A_e B_f C_g D_h E_i O_x \qquad (1)$$

(where: Mo is molybdenum; W is tungsten; Bi is bismuth; Fe is iron; A is at least one element selected from among cobalt and nickel; B is at least one element selected from among sodium, potassium, rubidium, cesium, and thallium; C is at least one element selected from among boron, phosphorus, chrome, manganese, zinc, arsenic, niobium, tin, antimony, tellurium, cerium, and lead; D is at least one element selected from among silicon, aluminum, titanium, and zirconium; E is at least one element selected from among alkaline earth metals; and O is oxygen; and further, a, b, c, d, e, f g, h, i, and x denote atomic ratios of Mo, W, Bi, Fe, A, B, C, D, E, and O respectively; and in the case of a=12, the following inequalities are satisfied: $0 \leq b \leq 5$; $0.1 \leq c \leq 10$; $0.1 \leq d \leq 20$; $1 \leq e \leq 20$; $0.001 \leq f \leq 5$; $0 \leq g \leq 10$; $0 \leq h \leq 30$; and $0 \leq i \leq 5$; and x is a numerical value as determined by the oxidation state of each element).

There is no especial limitation on starting raw materials of the above catalytic component elements. Ammonium salts, nitrate salts, carbonate salts, chlorides, sulfate salts, hydroxides, organic acid salts, and oxides of metal elements as generally used for this kind of catalyst or a mixture thereof in combination may be used, but the ammonium salts and nitrate salts are favorably used.

An aqueous solution or slurry of a blend of the starting materials for the catalyst may be prepared by a process as generally used for this kind of catalyst. For example, aqueous solutions may be prepared from the above raw materials for the catalyst and then blended together in order. There is no especial limitation on conditions for blending the raw materials for the catalyst (e g. blending order, temperature, pressure, and pH). There is also a case where the aqueous solution or slurry of the blend of the starting materials for the catalyst, as obtained in this way, is concentrated to dryness to obtain a cake solid, when the occasion demands. The aforementioned aqueous solution, aqueous slurry, or the cake solid of the blend of the starting materials for the catalyst is heat-treated, thus obtaining the catalyst precursor P1.

There is no especial limitation on the heat treatment method for obtaining the catalyst precursor P1 and the form of the catalyst precursor. For example, a powdery catalyst precursor may be obtained with such as a spray dryer and a drum dryer, or a blockish or flaky catalyst precursor may be obtained by heating under a gas stream with such as a box-type dryer or a tunnel-type dryer.

The heat-treatment conditions are set in such a manner that the ignition loss ratio of the catalyst precursor P1 will be in the range of 10 to 40 mass % (excluding 40 mass %), favorably 13 to 37 mass %, more favorably 15 to 35 mass %.

When the box-type dryer is, for example, used, the ignition loss ratio of the catalyst precursor P1 can be controlled by adjusting the temperature and/or linear velocity of a heated gas and/or the heat-treatment time. The higher the temperature of the heated gas is, or the faster the linear velocity of the heated gas is, or also the longer the heat-treatment time is, the smaller the ignition loss ratio of the catalyst precursor P1 can be made.

The ignition loss includes: such as a nitrate radical component and an ammonium radical component that remain in the catalyst precursor P1 and become decomposed, volatilized, and sublimed by the heat treatment; and water (The nitrate salts and the ammonium salts as contained in the catalyst precursor P1 become decomposed by heating at high temperature and thus removed from the catalyst precursor P1. That is to say, it is meant that: the higher the ignition loss ratio of the catalyst precursor is, the higher the content of such as the nitrate salts and the ammonium salts in this catalyst precursor is.).

The above heat-treatment conditions such as the temperature of the heated gas and the linear velocity of the heated gas should fitly be selected according to the kind or properties of a heating apparatus (dryer), and they cannot be specified sweepingly. However, the catalyst precursor may be obtained by such as carrying out heat treatment under a gas stream at a temperature of not higher than 230° C. for 3 to 24 hours.

In the case where the ignition loss ratio of the catalyst precursor P1 as obtained is not less than 40 mass %, it is favorable that: the conditions are changed, for example, in such a manner that the temperature of the heated gas will be changed, and then the heat treatment is carried out again, thereby adjusting the ignition loss ratio so as to be in the above range. In the case where a catalyst precursor P1 having an ignition loss ratio of not less than 40 mass % is used, the moldability is remarkably deteriorated in a subsequent molding step, and besides, the catalyst strength is also greatly lowered.

In the case where the ignition loss ratio of the catalyst precursor P1 is less than 10 mass %, the catalytic activity and the yield of the objective product tend to decrease.

The catalyst precursor P1 of which the ignition loss ratio has been adjusted in the above way is subjected to a pulverization step or a classification step for obtaining a powder having an appropriate particle diameter when the occasion demands, and then it is transferred to a subsequent molding step.

Into the catalyst precursor P1 of which the ignition loss ratio has been adjusted in the above range, a binder is subsequently added and mixed to thus prepare the catalyst precursor P2.

There is no especial limitation on the kind of the binder as added and mixed into the catalyst precursor P1. Examples thereof include publicly known binders usable for molding of catalysts, but water is favorable.

The amount of the binder as added and mixed into the catalyst precursor P1 (favorably the amount of the water as added and mixed into the catalyst precursor P1) is in the range of 5 to 30 parts by mass, favorably 8 to 27 parts by mass, more favorably 11 to 24 parts by mass, relative to 100 parts by mass of the aforementioned catalyst precursor P1.

In the case where the amount as added is larger than 30 parts by mass, there is also a case where: the moldability of the catalyst precursor P2 is deteriorated to such a degree that the molding cannot be carried out. In the case where the amount as added is smaller than 5 parts by mass, the binding between the catalyst precursors P2 is weak. Therefore, the molding itself cannot be carried out, or even if the molding can be carried out, the physical strength of the catalyst is lowered. In the case of carrying out extrusion-molding, a molding machine is broken if things come to the worst.

The water as added to the catalyst precursor P1 can be added even in the form of an aqueous solution of various substances or a mixture of various substances and water.

Examples of the substances as added together with the water include: molding assistants for enhancing the moldability; reinforcements and binders for enhancing the catalyst strength; and substances that are generally used as pore-forming agents for forming pores in the catalyst. As to these substances, favorable are substances that do not have bad influence on the catalyst performance (activity, and selectivity of the objective product) by the addition. That is to say, favorable are: (1) an aqueous solution, or a mixture with water, of a substance that does not remain in the catalyst after the calcination; and (2) an aqueous solution, or a mixture with water, of a substance that does not have bad influence on the catalyst performance even if this substance remains in the catalyst after the calcination.

Specific examples of the above (1) include: organic compounds, such as ethylene glycol, glycerin, propionic acid, maleic acid, benzyl alcohol, propyl alcohol, butyl alcohol, and phenol; and nitric acid, ammonium nitrate, and ammonium carbonate.

Specific examples of the above (2) include those which are generally known as reinforcements, such as silica, alumina, glass fibers, silicon carbide, and silicon nitride. In the present invention, the catalyst as produced has practically sufficient physical strength, but the above reinforcements are added thereto when the still higher physical strength is necessary.

In the case where the amount of the above substances as added is in excess, the physical strength of the catalyst is remarkably lowered, and therefore it is favorable to add them in such an amount not as does not lower the physical strength of the catalyst to such an extent that the catalyst cannot be practically used as an industrial catalyst.

When the water is added in the form of the above aqueous solution of various substances or mixture of various substances and water, for example, when the molding is carried out by adding 20 parts by mass of 5 mass % aqueous ethylene glycol solution to 100 parts by mass of the catalyst precursor P1, the amount of the water as added to the P1 is calculated as follows: $20 \times (1-0.05)=19$ parts by mass.

The catalyst as used in the present invention may be either a molded catalyst as obtained by molding the catalyst precursor P2 into a definite shape, or a supported catalyst as obtained by supporting the catalyst precursor P2 on any inert support having a definite shape, but the molded catalyst as obtained by molding the catalyst precursor P2 into a definite shape is favorable.

In the case of the supported catalyst, such as alumina, silica, silica-alumina, titania, magnesia, steatite, and silicon carbide can be used as the inert support.

The method for molding the catalyst may be a hitherto publicly known method. Applicable are molding methods such as an extrusion-molding method, a granulation method (tumbling granulation apparatuses, and centrifugal-fluid-coating apparatuses), and Marumerizer method. Of the above, the extrusion-molding method is favorable.

As to the shape of the catalyst, any shape such as a column shape, a ring shape, a spherical shape, and an irregular shape can be selected.

The average diameter of the catalyst is in the range of 1 to 15 mm, favorably 3 to 10 mm.

The molded structure as obtained is calcined under a gas stream in the temperature range of 350 to 600° C. (favorably 400 to 550° C.) for about 1 to about 10 hours, thus obtaining the objective catalyst for synthesis of an unsaturated aldehyde and/or an unsaturated carboxylic acid.

The catalyst as obtained in this way favorably has a ratio of the apparent density of the catalyst to the true density of the catalyst (apparent density of catalyst/true density of catalyst) in the range of 0.25 to 0.55, more favorably 0.30 to 0.50.

Incidentally, in the present invention, the apparent density of the catalyst is calculated as follows: apparent density of catalyst=1/(1/true density+pore volume).

In the case where the ratio of the apparent density of the catalyst to the true density of the catalyst is less than 0.25, there is a case where the diffusion efficiency in the pores rises together with the increase of the pore volume. In this case, the activity of the catalyst and the selectivity of the objective product are enhanced, but there is a disadvantage in that the catalyst strength is remarkably lowered.

In the case where the ratio of the apparent density of the catalyst to the true density of the catalyst is more than 0.55, contrary to the above, the catalyst strength is enhanced, but there is a disadvantage in that the activity of the catalyst and the selectivity of the objective product are remarkably lowered.

The pore volume of the catalyst is favorably in the range of 0.2 to 0.6 cm$^3$/g, more favorably 0.25 to 0.55 cm$^3$/g.

There is no especial limitation on the production process which comprises the step of carrying out catalytic gas phase oxidation of at least one compound selected from the group consisting of propylene, isobutylene, t-butyl alcohol, and methyl t-butyl ether as a raw material with molecular oxygen or a molecular-oxygen-containing gas, thereby producing the unsaturated aldehyde and/or the unsaturated carboxylic acid which correspond to the raw material, except for using the present invention catalyst as a catalyst. This production process can be carried out with generally used apparatuses, by generally used methods, and under generally used conditions.

As is mentioned above, the raw gas as used in the above production process for the unsaturated aldehyde and/or the unsaturated carboxylic acid is at least one compound selected from the group consisting of propylene, isobutylene, t-butyl alcohol, and methyl t-butyl ether, but the propylene is favorable from the viewpoint such that the effects of the present invention can be displayed still more. That is to say, the present invention catalyst is favorably used for a process in which the propylene is used as a raw gas, thereby producing acrolein (as the unsaturated aldehyde corresponding to the raw material) and acrylic acid (as the unsaturated carboxylic acid corresponding to the raw material). However, needless to say, the present invention catalyst is favorably used also for a process in which at least one compound selected from the group consisting of isobutylene, t-butyl alcohol, and methyl t-butyl ether is used as a raw material, thereby producing the unsaturated aldehyde and/or the unsaturated carboxylic acid that correspond to the raw material.

The catalytic gas phase reaction in the present invention may be carried out by a conventional one-pass method or recycling method, and such as fixed-bed reactors, fluidized-bed reactors, and moving-bed reactors can be used as reactors.

As to conditions of the above reaction, the reaction may be carried out, for example, by bringing a mixed gas into contact with the present invention catalyst in the temperature range of 250 to 450° C. under a pressure of 0.1 to 1 MPa at a space velocity of 300 to 5,000 hr$^{-1}$ (STP), wherein the mixed gas includes: 1 to 15 volume % of at least one compound selected from the group consisting of propylene, isobutylene, t-butyl alcohol, and methyl t-butyl ether as a raw gas; molecular oxygen having a volume ratio of 1 to 10 times relative to this raw gas; and an inert gas (e.g. water vapor, nitrogen gas, and carbon dioxide gas) as a diluent.

(Effects and Advantages of the Invention):

The present invention can provide: a production process for a catalyst for synthesis of an unsaturated aldehyde and/or an unsaturated carboxylic acid, which production process is suitable for producing the catalyst with good reproducibility, wherein the catalyst is excellent in activity, selectivity, and physical strength; a catalyst as obtained by this production process; and a process comprising the step of carrying out catalytic gas phase oxidation of at least one compound selected from the group consisting of propylene, isobutylene, t-butyl alcohol, and methyl t-butyl ether as a raw material with molecular oxygen or a molecular-oxygen-containing gas in the presence of the above catalyst, thereby producing the corresponding unsaturated aldehyde and/or unsaturated carboxylic acid. Therefore, the industrial value of utilization of the present invention is extremely large.

DETAILED DESCRIPTION OF THE PREFERRED EMBODIMENTS

Hereinafter, the present invention is more specifically illustrated by the following examples of some preferred embodiments. However, the present invention is not limited to these examples in any way.

Incidentally, herein each of the conversion, selectivity, and yield is defined as follows.

Conversion (mol %)=(mols of reacted starting raw material)/(mols of supplied starting raw material) ×100

Selectivity (mol %)=(mols of produced unsaturated aldehyde and carboxylic acid)/(mols of reacted starting raw material)×100

Yield (mol %)=(mols of produced unsaturated aldehyde and carboxylic acid)/(mols of supplied starting raw material)×100

In addition, the true density and the pore volume of the catalyst were measured with the following apparatuses:

Measurement apparatus of true density: AutoPycnometer 1320 produced by Micromeritics Co., Ltd.

Measurement apparatus of pore volume: AutoPoreIII produced by Micromeritics Co., Ltd.

In addition, in the present invention, a value as measured by a method below is used as an index for representing the physical strength of the catalyst.

(Measurement Method for Catalyst Strength):

A stainless-steel-made reaction tube of 25 mm in inner diameter and 5,000 mm in length is settled in a vertical direction, and the lower end of the above reaction tube is sealed with a stainless-steel-made receiving plate of 1 mm in thickness. After about 50 g of catalyst is dropped from the upper end of the reaction tube into the reaction tube, the stainless-steel-made receiving plate as placed at the lower end of the reaction tube is removed, and then the catalyst is quietly extracted from the reaction tube. The catalyst as extracted is classified with a sieve having a mesh opening size of 5 mm, and the mass of the catalyst remaining on the sieve is weighed.

Catalyst strength (mass %)=(mass of catalyst remaining on sieve)/(mass of catalyst as dropped from upper end of reaction tube)×100

That is to say, the higher the value is, the higher the catalyst strength is.

CATALYST PRODUCTION EXAMPLE 1

Preparation of Catalyst (1)

While 10 L of pure water was heat-stirred, 1,500 g of ammonium molybdate and 96 g of ammonium paratungstate were dissolved therein, and 425 g of 20 mass % silica sol was further added thereto. To this mixed liquid, a liquid as obtained by dissolving 1,030 g of cobalt nitrate, 618 g of nickel nitrate, 229 g of iron nitrate, and 5.7 g of potassium nitrate into 1,000 ml of pure water was dropwise added under vigorously stirred conditions. Subsequently, a liquid as obtained by dissolving 446 g of bismuth nitrate into an aqueous solution was dropwise added thereto under vigorously stirred conditions, wherein the aqueous solution was obtained by adding 250 ml of concentrated nitric acid to 500 ml of pure water. Then, the suspension as produced was heat-stirred, and thereby the major part of the water was evaporated, thus obtaining a cake solid. The cake solid as obtained was heat-treated with a box-type dryer (temperature of heated gas: 170° C., linear velocity of heated gas: 1.0 m/sec, and heat-treatment time: 12 hours), thus obtaining a blockish catalyst precursor. This catalyst precursor was pulverized, and thereafter its ignition loss ratio was measured. As a result, it was 19.8 mass %. Next, pure water was added to the resultant catalyst precursor powder in a ratio of 150 g of the water to 1 kg of the catalyst precursor powder, and the resultant mixture was kneaded for 1 hour, and thereafter the mixture was extrusion-molded into a ring shape of 6 mm in outer diameter, 2 mm in inner diameter, and 6 mm in height. Next, the resultant molded structure was calcined under a stream of air at 470° C. for 5 hours, thus obtaining a catalyst (1). The composition of metal elements in this catalyst except for oxygen was as follows:

catalyst (1): $Mo_{12}W_{0.5}Co_5Ni_3Bi_{1.3}Fe_{0.8}Si_2K_{0.08}$.

In addition, the catalyst (1) had a ratio of its apparent density to its true density (apparent density of catalyst/true density of catalyst) of 0.37, and further had a catalyst strength of 98.3 mass %.

As to the catalyst (1), the heat-treatment conditions, the ignition loss ratio of the catalyst precursor P1, the kind of binder, the amount of the binder as added relative to 100 parts by mass of the catalyst precursor P1, the amount of the water as added relative to 100 parts by mass of the catalyst precursor P1, the ratio of the apparent density to the true density (apparent density of catalyst/true density of catalyst), and the catalyst strength are summarized in Table 1.

CATALYST PRODUCTION EXAMPLE 2

Preparation of Catalyst (2)

In order to confirm the reproducibility, a catalyst (2) was obtained in the same way as of Catalyst Production Example 1.

As to the catalyst (2), the heat-treatment conditions, the ignition loss ratio of the catalyst precursor P1, the kind of binder, the amount of the binder as added relative to 100 parts by mass of the catalyst precursor P1, the amount of the water as added relative to 100 parts by mass of the catalyst precursor P1, the ratio of the apparent density to the true density (apparent density of catalyst/true density of catalyst), and the catalyst strength are summarized in Table 1.

CATALYST PRODUCTION EXAMPLES 3 TO 11

Preparation of Catalysts (3) to (11)

Catalysts (3) to (11) were obtained respectively in the same way as of Catalyst Production Example 1 except that: the heat-treatment conditions (temperature of heated gas, linear velocity of heated gas, and heat-treatment time) of the cake solid, and the amount of the binder as added were changed in the preparation method of the catalyst (1) in the above Catalyst Production Example 1.

As to the catalysts (3) to (11), the heat-treatment conditions, the ignition loss ratio of the catalyst precursor P1, the kind of binder, the amount of the binder as added relative to 100 parts by mass of the catalyst precursor P1, the amount of the water as added relative to 100 parts by mass of the catalyst precursor P1, the ratio of the apparent density to the true density (apparent density of catalyst/true density of catalyst), and the catalyst strength are summarized in Table 1.

CATALYST PRODUCTION EXAMPLE 12

Preparation of Catalyst (12)

While 10 L of pure water was heat-stirred, 1,500 g of ammonium molybdate and 96 g of ammonium paratungstate were dissolved therein, and 213 g of 20 mass % silica sol was further added thereto. To this mixed liquid, a liquid as obtained by dissolving 1,360 g of cobalt nitrate, 206 g of nickel nitrate, 372 g of iron nitrate, and 4.3 g of potassium nitrate into 1,000 ml of pure water was dropwise added under vigorously stirred conditions. Subsequently, a liquid as obtained by dissolving 446 g of bismuth nitrate into an aqueous solution was dropwise added thereto under vigorously stirred conditions, wherein the aqueous solution was obtained by adding 250 ml of concentrated nitric acid to 500 ml of pure water. Then, the suspension as produced was heat-stirred, and thereby the major part of the water was evaporated, thus obtaining a cake solid. The cake solid as obtained was heat-treated with a box-type dryer (temperature of heated gas: 170° C., linear velocity of heated gas: 1.0 m/sec, and heat-treatment time: 12 hours), thus obtaining a blockish catalyst precursor. This catalyst precursor was pulverized, and thereafter its ignition loss ratio was measured. As a result, it was 19.9 mass %. Next, 50 mass % aqueous ammonium nitrate solution was added to the resultant catalyst precursor powder in a ratio of 280 g of the aqueous solution to 1 kg of the catalyst precursor powder, and the resultant mixture was kneaded for 1 hour, and thereafter the mixture was extrusion-molded into a ring shape of 6 mm in outer diameter, 2 mm in inner diameter, and 6 mm in height. Next, the resultant molded structure was calcined under a stream of air at 480° C. for 5 hours, thus obtaining a catalyst (12). The composition of metal elements in this catalyst except for oxygen was as follows:

catalyst (12): $Mo_{12}W_{0.5}Co_{6.6}Ni_1Bi_{1.3}Fe_{1.3}Si_1K_{0.06}$.

As to the catalyst (12), the heat-treatment conditions, the ignition loss ratio of the catalyst precursor P1, the kind of binder, the amount of the binder as added relative to 100 parts by mass of the catalyst precursor P1, the amount of the water as added relative to 100 parts by mass of the catalyst precursor P1, the ratio of the apparent density to the true density (apparent density of catalyst/true density of catalyst), and the catalyst strength are summarized in Table 1.

CATALYST PRODUCTION EXAMPLES 13 AND 14

Preparation of Catalysts (13) and (14)

Catalysts (13) and (14) were obtained respectively in the same way as of Catalyst Production Example 12 except that the amount of the binder as added was changed in the preparation method of the catalyst (12) in the above Catalyst Production Example 12.

As to the catalysts (13) and (14), the heat-treatment conditions, the ignition loss ratio of the catalyst precursor P1, the kind of binder, the amount of the binder as added relative to 100 parts by mass of the catalyst precursor P1, the amount of the water as added relative to 100 parts by mass of the catalyst precursor P1, the ratio of the apparent density to the true density (apparent density of catalyst/true density of catalyst), and the catalyst strength are summarized in Table 1.

CATALYST PRODUCTION EXAMPLE 15

Preparation of Catalyst (15)

A catalyst precursor powder was obtained in the same way as of the preparation method of the catalyst (12) in the above Catalyst Production Example 12. This catalyst precursor powder was pulverized, and thereafter 50 mass % aqueous ammonium nitrate solution was added to the catalyst precursor powder in a ratio of 600 g of the aqueous solution to 1 kg of the catalyst precursor powder, and the resultant mixture was kneaded for 1 hour, and thereafter an attempt was made to extrusion-mold the mixture into a ring shape of 6 mm in outer diameter, 2 mm in inner diameter, and 6 mm in height. However, the viscosity of the catalyst precursor rose to such an extent that the molding could not be carried out, and therefore the molding was stopped.

CATALYST PRODUCTION EXAMPLE 16

Preparation of Catalyst (16)

A catalyst precursor powder was obtained in the same way as of the preparation method of the catalyst (12) in the above Catalyst Production Example 12. This catalyst precursor powder was pulverized, and thereafter 50 mass % aqueous ammonium nitrate solution was added to the catalyst precursor powder in a ratio of 90 g of the aqueous solution to 1 kg of the catalyst precursor powder, and the resultant mixture was kneaded for 1 hour, and thereafter an attempt was made to extrusion-mold the mixture into a ring shape of 6 mm in outer diameter, 2 mm in inner diameter, and 6 mm in height. However, extraordinary noises were made from a molding machine, and extraordinary vibrations also occurred, and therefore the molding was stopped.

CATALYST PRODUCTION EXAMPLE 17

Preparation of Catalyst (17)

While 10 L of pure water was heat-stirred, 1,500 g of ammonium molybdate and 382 g of ammonium paratungstate were dissolved therein, and 213 g of 20 mass % silica sol was further added thereto. To this mixed liquid, a liquid as obtained by dissolving 1,442 g of cobalt nitrate, 429 g of ferric nitrate, and 83 g of cesium nitrate into 1,000 ml of pure water was dropwise added under vigorously stirred conditions. Subsequently, a liquid as obtained by dissolving 515 g of bismuth nitrate into an aqueous acidic solution was dropwise added thereto under vigorously stirred conditions, wherein the aqueous acidic solution was obtained by adding 250 ml of concentrated nitric acid to 500 ml of pure water. Then, the suspension as produced was heat-stirred, and thereby the major part of the water was evaporated, thus obtaining a cake solid. The cake solid as obtained was heat-treated with a box-type dryer (temperature of heated gas: 170° C., linear velocity of heated gas: 1.0 m/sec, and heat-treatment time: 12 hours), thus obtaining a blockish catalyst precursor. This catalyst precursor was pulverized, and thereafter its ignition loss ratio was measured. As a result, it was 21.0 mass %. Next, 50 mass % aqueous ammonium nitrate solution was added to the resultant catalyst precursor powder in a ratio of 230 g of the aqueous solution to 1 kg of the catalyst precursor powder, and the resultant mixture was kneaded for 1 hour, and thereafter the mixture was extrusion-molded into a ring shape of 5.5 mm in outer diameter, 2 mm in inner diameter, and 5.5 mm in height. Next, the resultant molded structure was calcined under a stream of air at 500° C. for 5 hours, thus obtaining a catalyst (17). The composition of metal elements in this catalyst except for oxygen was as follows:

catalyst (17): $Mo_{12}W_2Co_7Bi_{1.5}Fe_{1.5}Si_1Cs_{0.6}$.

As to the catalyst (17), the heat-treatment conditions, the ignition loss ratio of the catalyst precursor P1, the kind of binder, the amount of the binder as added relative to 100 parts by mass of the catalyst precursor P1, the amount of the water as added relative to 100 parts by mass of the catalyst precursor P1, the ratio of the apparent density to the true density (apparent density of catalyst/true density of catalyst), and the catalyst strength are summarized in Table 1.

TABLE 1

| Catalyst Production Example | Catalyst number | Heat-treatment conditions | | | Catalyst precursor P1 Ignition loss ratio (mass %) | Binder | | Amount of water as added (parts by mass) | Apparent density of catalyst/true density of catalyst | Catalyst strength (mass %) |
| | | Temperature of heated gas (° C.) | Linear velocity of heated gas (m/sec) | Heat-treatment time (hours) | | Kind | Amount as added (parts by mass) | | | |
| --- | --- | --- | --- | --- | --- | --- | --- | --- | --- | --- |
| 1 | (1) | 170 | 1.0 | 12 | 19.8 | Pure water | 15 | 15 | 0.37 | 98.3 |
| 2 | (2) | 170 | 1.0 | 12 | 19.6 | Pure water | 15 | 15 | 0.37 | 98.5 |
| 3 | (3) | 170 | 1.0 | 5 | 40.5 | Pure water | 7 | 7 | 0.24 | 95.2 |
| 4 | (4) | 170 | 1.0 | 20 | 14.7 | Pure water | 17 | 17 | 0.42 | 98.6 |
| 5 | (5) | 170 | 0.7 | 12 | 29.8 | Pure water | 11 | 11 | 0.31 | 98.0 |
| 6 | (6) | 170 | 1.3 | 12 | 15.3 | Pure water | 17 | 17 | 0.43 | 98.3 |
| 7 | (7) | 130 | 1.3 | 24 | 35.6 | Pure water | 9 | 9 | 0.29 | 97.7 |

TABLE 1-continued

| Catalyst Production Example | Catalyst number | Heat-treatment conditions | | | Catalyst precursor P1 Ignition loss ratio (mass %) | Binder | | | Apparent density of catalyst/true density of catalyst | Catalyst strength (mass %) |
|---|---|---|---|---|---|---|---|---|---|---|
| | | Temperature of heated gas (° C.) | Linear velocity of heated gas (m/sec) | Heat-treatment time (hours) | | Kind | Amount as added (parts by mass) | of water as added (parts by mass) | | |
| 8 | (8) | 130 | 1.0 | 10 | 40.8 | Pure water | 7 | 7 | 0.24 | 95.6 |
| 9 | (9) | 130 | 1.0 | 10 | 41.9 | Pure water | 7 | 7 | 0.23 | 95.3 |
| 10 | (10) | 210 | 0.6 | 8 | 11.8 | Pure water | 19 | 19 | 0.48 | 98.9 |
| 11 | (11) | 210 | 1.0 | 15 | 4.4 | Pure water | 21 | 21 | 0.57 | 99.1 |
| 12 | (12) | 170 | 1.0 | 12 | 19.9 | AN* | 28 | 14 | 0.33 | 97.4 |
| 13 | (13) | 170 | 1.0 | 12 | 19.6 | AN* | 50 | 25 | 0.27 | 96.4 |
| 14 | (14) | 170 | 1.0 | 12 | 19.5 | AN* | 14 | 7 | 0.47 | 98.5 |
| 15 | (15) | 170 | 1.0 | 12 | 20.0 | AN* | 60 | 30 | Impossible to mold | |
| 16 | (16) | 170 | 1.0 | 12 | 19.7 | AN* | 9 | 4.5 | Impossible to mold | |
| 17 | (17) | 170 | 1.0 | 12 | 20.0 | AN* | 23 | 11.5 | 0.34 | 97.0 |

*50 mass % aqueous ammonium nitrate solution

EXAMPLES 1 TO 10 AND COMPARATIVE EXAMPLES 1 to 4

Each of the catalysts (1) to (14) as obtained in Catalyst Production Examples 1 to 14 was packed into a stainless-steel-made reaction tube of 25 mm in inner diameter as heated with a molten nitrate salt in such a manner that the layer length would be 1,000 mm, and then a catalytic gas phase oxidation reaction of propylene was carried out by introducing a reaction gas having the following composition at a space velocity of 1,500 hr$^{-1}$ (STP). The results are listed in Table 2.
Propylene: 6 volume %
Air: 55 volume %
Water vapor: 30 volume %
Nitrogen: 9 volume %

EXAMPLE 11

The catalyst (17) as obtained in Catalyst Production Example 17 was packed into a stainless-steel-made reaction tube of 25 mm in inner diameter as heated with a molten nitrate salt in such a manner that the layer length would be 1,000 mm, and then a catalytic gas phase oxidation reaction of isobutylene was carried out by introducing a reaction gas having the following composition at a space velocity of 1,500 hr$^{-1}$ (STP).
Isobutylene: 6 volume %
Air: 65 volume %
Water vapor: 10 volume %
Nitrogen: 19 volume %
At a reaction temperature of 340° C., the conversion of the isobutylene, the total yield of methacrolein and methacrylic

TABLE 2

| | Catalyst number | Apparent density of catalyst/true density of catalyst | Catalyst strength (mass %) | Reaction temperature (° C.) | Conversion of propylene (mol %) | Total yield of acrolein and acrylic acid (mol %) | Total selectivity of acrolein and acrylic acid (mol %) |
|---|---|---|---|---|---|---|---|
| Example 1 | (1) | 0.37 | 98.3 | 310 | 98.2 | 92.2 | 93.9 |
| Example 2 | (2) | 0.37 | 98.5 | 310 | 98.2 | 92.4 | 94.1 |
| Comparative Example 1 | (3) | 0.24 | 95.2 | 310 | 98.4 | 91.9 | 93.4 |
| Example 3 | (4) | 0.42 | 98.6 | 310 | 97.6 | 91.8 | 94.1 |
| Example 4 | (5) | 0.31 | 98.0 | 310 | 98.4 | 92.0 | 93.5 |
| Example 5 | (6) | 0.43 | 98.3 | 310 | 97.6 | 91.9 | 94.2 |
| Example 6 | (7) | 0.29 | 97.7 | 310 | 98.4 | 91.9 | 93.4 |
| Comparative Example 2 | (8) | 0.24 | 95.6 | 310 | 98.0 | 91.8 | 93.7 |
| Comparative Example 3 | (9) | 0.23 | 95.3 | 310 | 98.1 | 91.2 | 93.0 |
| Example 7 | (10) | 0.48 | 98.9 | 310 | 97.2 | 91.2 | 93.8 |
| Comparative Example 4 | (11) | 0.57 | 99.1 | 310 | 94.6 | 88.9 | 94.0 |
| Example 8 | (12) | 0.33 | 97.4 | 310 | 98.4 | 92.4 | 93.9 |
| Example 9 | (13) | 0.27 | 96.4 | 310 | 98.7 | 92.3 | 93.5 |
| Example 10 | (14) | 0.47 | 98.5 | 310 | 97.7 | 91.8 | 94.0 | acid, and the total selectivity of methacrolein and methacrylic acid were 98.1 mol %, 86.5 mol %, and 88.2 mol % respectively.

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A process for preparing an unsaturated aldehyde and/or an unsaturated carboxylic acid, which comprises the step of carrying out catalytic gas phase oxidation, with a catalyst, of at least one compound selected from the group consisting of propylene, isobutylene, t-butyl alcohol, and methyl t-butyl ether as a raw material, with molecular oxygen or a molecular-oxygen-containing gas, thereby producing the unsaturated aldehyde and/or the unsaturated carboxylic acid which corresponds to the raw material;

with said catalyst being produced by a preliminary production process which comprises the steps of: carrying out heat treatment of an aqueous solution or slurry of a starting material to thus prepare a catalyst precursor P1, wherein the starting material includes molybdenum, bismuth, and iron as essential components; thereafter adding and mixing a binder into the catalyst precursor P1 to thus prepare a catalyst precursor P2; and molding and then calcining the catalyst precursor P2, thereby producing the catalyst for synthesis of the unsaturated aldehyde and/or the unsaturated carboxylic acid;

with the preliminary production process involving the step of controlling an ignition loss ratio of the catalyst precursor P1 in the range of 10 to 40 mass % (excluding 40 mass %) by adjusting at least one of a temperature of a heated gas, a linear velocity of a heated gas, and a heat-treatment time in carrying out said heat treatment of an aqueous solution or slurry of a starting material, and, when the catalyst precursor P1 is heated under air atmosphere at 300° C. for 1 hour, the ignition loss ratio of the catalyst precursor P1 is calculated from the following equation:

ignition loss ratio (mass %)=((mass of catalyst precursor P1 which has been prepared by said step of carrying out heat treatment of said aqueous solution or slurry of said starting material)−(mass of catalyst precursor P1 after catalyst precursor P1 has been heated under air atmosphere at 300° C. for 1 hour))/(mass of catalyst precursor P1 which has been prepared by said step of carrying out heat treatment of said aqueous solution or slurry of said starting material)×100.

2. An aldehyde/acid production process according to claim 1, wherein water is added and mixed as the binder in an amount of 5 to 30 parts by mass relative to 100 parts by mass of the catalyst precursor P1.

3. An aldehyde/acid production process according to claim 1, wherein said catalyst has a ratio of the apparent density of the catalyst to the true density of the catalyst (apparent density of catalyst/true density of catalyst) in a range of 0.25 to 0.55.

* * * * *